(12) United States Patent
Itagaki et al.

(10) Patent No.: US 6,410,741 B1
(45) Date of Patent: Jun. 25, 2002

(54) OPTICALLY ACTIVE BISOXAZOLINE COMPOUNDS, PRODUCTION AND USE THEREOF

(75) Inventors: Makoto Itagaki, Takatsuki; Gohfu Suzukamo, Suita, both of (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 09/563,914

(22) Filed: May 4, 2000

Related U.S. Application Data

(62) Division of application No. 09/128,971, filed on Aug. 4, 1998, now Pat. No. 6,072,081.

(30) Foreign Application Priority Data

Aug. 5, 1997 (JP) .............................................. 9-210417

(51) Int. Cl.⁷ .......................................... C07D 263/08

(52) U.S. Cl. .................................................... 548/237

(58) Field of Search ........................ 548/237; 562/506; 554/221, 214

(56) References Cited

PUBLICATIONS

Desmoni et al., Tetrahedron., vol 52, No. 43, pp. 13649–13654, 1996.*
Denmark et al., J. Org. Chem., 60, pp. 4884–4892, 1995.*
E. J. Corey et al., Highly enantioselective catalytic Diels–Alder addition promoted by a chiral bis(oxazline)–magnesium complex, vol. 33, No. 45, 1992, pp. 6807–6810; *Tetrahedron Letters*.
S. E. Denmark et al., Cyclopropanation with Diazomethane and Bis (oxazoline)palladium(II) Complexes, vol. 62 No. 10, 1997, pp. 3375–3389, *J. Org. Chem.*
S. Bennett et al., Structure and Mechanism in Aerobic Alkene Epoxidations promoted by Ruthenium Complexes Bis(dihydrooxazole) Ligands., vol. 3, 1995, pp. 367–376, J. Chem. Soc. Dalton Trans.
M. P. Doyle et al., Enantioselektive Synthese von makrocyclischen Lactonen durch intramolekulare Cyclopropanierrung von Diazoacetaten mit chiralen Cu(I)– und Rh(II)–Katalysatoren., vol. 108, No. 12, 1996, pp. 1439–1440, Angew. Chem.
A. V. Bedekar et al., A New Class of Bis–Oxazoline Ligands for the Cu–Catalysed Asymmetric Cyclopropanatio of Olefins. vol. 37, No. 23, 1996, pp. 4073–4076, *Tetrahedron Letters.*
U. Leutenegger et al., 5–Aza–Semicorrins: A New Class of Bidentate Nitrogen Ligands for Enantioselective Catalysis. vol. 48, No. 11, 1992, pp. 2143–2156, *Tetrahedron.*
R. E. Lowenthal et al., Asymmetric 1–8 Copper–Catalyzed Cyclopropanation of Ttrisubstituted and Unsymmetrical cis–1, 2–Disubstituted Olefins: Modified Bis–Oxazoline Ligands. vol. 32, No. 50, 1991, pp. 7373–7376, *Tetrahedron Letters.*
D. Müller et al., C(2)–Symmetric 4,4',5,5'–Tetrahydro–bis(Oxazoles) and 4,4',5,5'–Tetrahydro–2, 2'–methylenebis'oxa zoles! as Chiral Ligands for Enantioselective Catalysis. vol. 74, No. 1, 1991, pp. 232–240, *Helv. Chem. Act.*
A. Bernardi et al., Enantioselective Mukaiyama–Michael Reactions of 2–Carbomethoxycyclopentenone Catalyzed by Chiral Bis(Oxazoline)–Cu(II) Complexes. vol. 37, No. 49, 1996, pp. 8921–8924, *Tetrahedron Letters.*
H. Brunner et al., Asymmetric catalysis, 1–8 part 108. Copper catalysts with optically active ligands in the enantioselective Meerwein arylation of activated olefins. vol. 541, No. 1–2, 1997, pp. 89–95, *J. Organomet. Chem.*
J. M. Takasc et al., Enantioselective Diels–Alder reactions: room temperature bis(oxazoline)–zinc, –magnesium, and – copper triflate catalysts. vol. 8, No. 18, 1997, pp. 3073–3078, *Tetrahedron, Asymmetry.*
H. Falk et al., On the Chemistry of 1–8 Pyrrole Pigments, XCI: Coppoer Complexes of Pyridinologous Linear Tr and Tetra–pyrroles as Cyclopropanation Catalysts. vol. 125, No. 3, 1994, pp. 325–334, *Monatsh. Chem.*
Aratani, *Pure & Appl. Chem.*, vol. 57, No. 12, pp. 1839–1844 (1985).
Fritschi et al., *Helvetica Chimica Acta*, vol. 71, pp. 1553–1565 (1988).

(List continued on next page.)

*Primary Examiner*—Brenda Coleman
(74) *Attorney, Agent, or Firm*—Birch, Stewart, Kolasch & Birch, LLP

(57) ABSTRACT

An optically active bisoxazoline compound of the formula [I]:

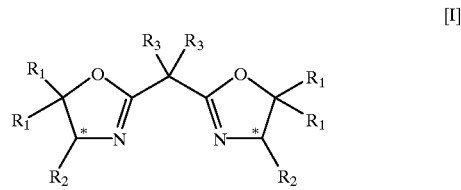

wherein $R_1$ represents alkyl group, cycloalkyl group, aralkyl group, phenyl group which may be substituted or alkoxy group and two geminal alkyl groups may be joined together to form a cyclic structure;

$R_2$ represents alkyl group, cycloalkyl group, aralkyl group, phenyl group which may be substituted;

$R_3$ represents hydrogen atom, (C2–C4)alkyl group or cycloalkyl group; and the asterisk * represents an asymmetric carbon atom

9 Claims, No Drawings

OTHER PUBLICATIONS

Lowenthal et al., *Tetrahedron Letters*, vol. 31, No. 42, pp. 6005–6008 (1990).

Evans et al., *J. Am. Chem. Soc.*, vol. 113, pp. 726–728 (1991).

Kanemasa et al., *Tetrahedron Letters*, vol. 35, No. 43, pp. 7985–7988 (1994).

Gant et al., *Tetrahedron Letters*, vol. 36, No. 48, pp. 8745–8748 (1995).

* cited by examiner

OPTICALLY ACTIVE BISOXAZOLINE COMPOUNDS, PRODUCTION AND USE THEREOF

This application is a divisional of application Ser. No. 09/128,971, filed on Aug. 4, 1998, now U.S. Pat. No. 6,072,081 the entire contents of which are hereby incorporated by reference.

BACKGROUND OF THE INVENTION

1. Field of the Invention

The present invention relates to optically active bisoxazoline compounds, a process for producing them and a process for producing optically active cyclopropanecarboxylic acid derivatives using them.

2. Description of Related Arts

The optically active cyclopropanecarboxylic acid esters are important compounds as intermediates for pharmaceuticals and pesticides. For example, (+)-2,2-dimethyl-3-(2-methyl-1-propenyl)cyclopropanecarboxylic acid, also known as chrysanthemum-monocarboxylic acid, constitutes the acid component of synthetic pyrethroid insecticides.

Conventionally, as the methods for directly producing optically active cyclopropanecarboxylic acid esters by synthetic technique, for example, a method has been known in which a prochiral olefin is reacted with a diazoacetic acid ester in the presence of an asymmetric copper complex using an optically active bis[2-(4,5-diphenyl-1,3-oxazolinyl)]methane as the ligand (Tetrahedron Lett., 32, 7373 (1991)).

Since, however, this method has problems that the raw material used for synthesizing the ligand is expensive and that the method for synthesizing the ligand is complicated, this method can not always be said to be an industrially advantageous method.

The present inventors have completed the present invention as the result of an extensive study conducted for the purpose of providing optically active bisoxazoline compounds useful as asymmetric ligands for copper complexes which are used in preparing optically active cyclopropanecarboxylic acid esters by reacting an olefin with a diazoacetic acid ester.

SUMMARY OF THE INVENTION

The present invention provides:

1. an optically active bisoxazoline compound of the formula [I]:

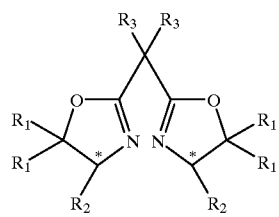

[I]

wherein
$R_1$ represents alkyl group, cycloalkyl group, aralkyl group, phenyl group which may be substituted or alkoxy group and the geminal alkyl groups may be joined together to form a cyclic structure;
$R_2$ represents alkyl group, cycloalkyl group, aralkyl group, or phenyl group which may be substituted,
$R_3$ represents a hydrogen atom, (C2–C4)alkyl group or cycloalkyl group and the asterisk * represents an asymmetric carbon atom;

2. a process for producing the optically active bisoxazoline compound of the formula [I] which comprises reacting an optically active 2-amino alcohol of the formula [II]:

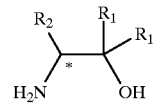

[II]

wherein $R_1$, $R_2$ and the asterisk * are as defined above, with a malonic acid derivative of the formula (3):

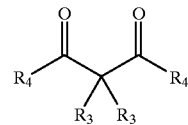

[III]

wherein $R_3$ is as defined above and $R_4$ represents alkoxy group or halogen atom, to give a bisamido alcohol compound of the formula [IV]:

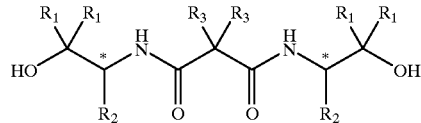

[IV]

wherein $R_1$, $R_2$ and $R_3$ are as defined above, and then subjecting the compound of the formula [IV] to cyclization reaction in the presence of a Lewis acid catalyst; and 3. a process for producing an optically active cyclopropanecarboxylic acid derivative of the formula [VII]:

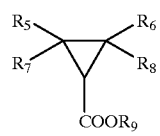

[VII]

wherein $R_5$, $R_6$, $R_7$ and $R_8$ are the same or different and represent hydrogen atom, halogen atom, alkyl group, aralkyl group, aryl group, alkenyl group, alkyl group substituted with halogen atom or alkenyl group substituted with halogen atom, with the proviso that when $R_5$ and $R_6$ represent the same group, then $R_7$ and $R_3$ represent different groups, and $R_9$ represents alkyl group, cycloalkyl group or phenyl group which may be substituted, which comprises reacting a prochiral olefin of the formula [V]:

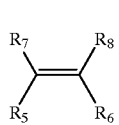

wherein $R_5$, $R_6$, $R_7$ and $R_8$ are as defined above, with a diazoacetic acid ester of the formula [VI]:

wherein $R_9$ is as defined above, in the presence of a copper complex prepared from an optically active bisoxazoline compound of the formula [I] and a copper compound.

DETAILED DESCRIPTION

In the optically active bisoxazoline compounds [I] according to the present invention, the alkyl group represented by $R_1$ and $R_2$ includes methyl group, ethyl group, n-propyl group, isopropyl group, n-butyl group, t-butyl group, n-amyl group, neopentyl group, n-hexyl group, n-octyl group, n-nonyl group and the like, and the cycloalkyl group includes cyclohexyl group, menthyl group and the like.

Examples of the (C2–C4)alkyl group for $R_3$ includes an ethyl, n-propyl group, n-butyl group, isobutyl group.

When $R_1$ is alkyl group, two geminal alkyl groups may be joined together to form a cyclic structure containing 4 to 7 carbon atoms.

In the substituent $R_1$, the alkoxy group includes methoxy group, ethoxy group, n-propoxy group, t-butoxy group and the like. The aralkyl group includes benzyl group, 2-phenylethyl group, 2-naphthylethyl group, diphenylmethyl group and the like. The phenyl group which may be substituted includes phenyl group, alkylphenyl group, alkoxyphenyl group, alkylalkoxyphenyl group and the like. These alkylphenyl group, alkoxyphenyl group, alkylalkoxyphenyl group include, for example, phenyl group substituted with 1–3 alkyl and/or alkoxy groups, respectively, described above at ortho-, meta- or para-position.

The optically active bisoxazoline compounds [I] according to the present invention have two asymmetric carbon atoms, as indicated by the asterisk *, and include at least two kinds of optical isomers resulting from the asymmetric carbon atoms. The optically active bisoxazoline compounds [I] according to the present invention contain such optical isomers.

The optically active bisoxazoline compounds [I] according to the present invention are novel, and can be synthesized, for example, by the following process.

The optically active bisoxazoline compound [I] can be obtained by reacting an optically active 2-amino alcohol of the formula [II]:

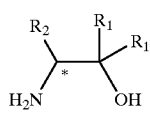

wherein $R_1$, $R_2$ and the asterisk * are as defined above, with a malonic acid derivative of the formula [III]:

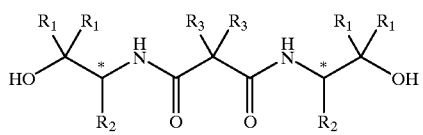

wherein $R_3$ is as defined above and $R_4$ represents alkoxy group or halogen atom, to give a bisamido alcohol compound of the formula [IV]:

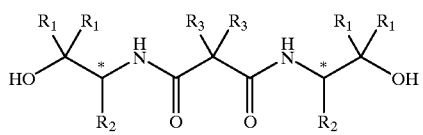

wherein $R_1$, $R_2$ and $R_3$ are as defined above, and then subjecting this compound to cyclization in the presence of a Lewis acid catalyst.

The optically active 2-amino alcohol [II] includes: for example,
(R)-2-amino-1,1-dimethylpropanol,
(R)-2-amino-1,1-diethylpropanol,
(R)-2-amino-1,1-di-n-propylpropanol,
(R)-2-amino-1,1-di-i-propylpropanol,
(R)-2-amino-1,1-dicyclohexylpropanol,
(R)-2-amino-1,1-dimethoxypropanol,
(R)-2-amino-1,1-diethoxypropanol,
(R)-2-amino-1,1-diphenylpropanol,
(R)-2-amino-1,1-di-(2-methylphenyl)propanol,
(R)-2-amino-1,1-di-(3-methylphenyl)propanol,
(R)-2-amino-1,1-di-(4-methylphenyl)propanol,
(R)-2-amino-1,1 di-(2-methoxyphenyl)propanol,
(R)-2-amino-1,1-di-(3-methoxyphenyl)propanol,
(R)-2-amino-1,1-di-(4-methoxyphenyl)propanol,
1-(1-(R)-aminoethyl)cyclobutanol,
1-(1-(R)-aminoethyl)cyclopentanol,
1-(1-(R)-aminoethyl)cyclohexanol,
1-(1-(R)-aminoethyl)cycloheptanol,
(R)-2-amino-3-methyl-1,1-dimethylbutanol,
(R)-2-amino-3-methyl-1,1-diethylbutanol,
(R)-2-amino-3-methyl-1,1-di-n-propylbutanol,
(R)-2-amino-3-methyl-1,1-di-i-propylbutanol,
(R)-2-amino-3-methyl-1,1-dicyclohexylbutanol,
(R)-2-amino-3-methyl-1,1-diphenylbutanol,
(R)-2-amino-3-methyl-1,1-di-(2-methylphenyl)butanol,
(R)-2-amino-3-methyl-1,1-di-(3-methylphenyl)butanol,
(R)-2-amino-3-methyl-1,1-di-(4-methylphenyl)butanol,
(R)-2-amino-3-methyl-1,1-di-(2-methoxyphenyl)butanol,
(R)-2-amino-3-methyl-1,1-di-(3-methoxyphenyl)butanol,
(R)-2-amino-3-methyl-1,1-di-(4-methoxyphenyl)butanol,
1-(1-(R)-amino-2-methyl-n-propyl)cyclobutanol,
1-(1-(R)-amino-2-methyl-n-propyl)cyclopentanol,
1-(1-(R)-amino-2-methyl-n-propyl)cyclohexanol,
1-(1-(R)-amino-2-methyl-n-propyl)cycloheptanol,
(R)-2-amino-4-methyl-1,1-dimethylpentanol,
(R)-2-amino-4-methyl-1,1-diethylpentanol,
(R)-2-amino-4-methyl-1,1-di-n-propylpentanol,
(R)-2-amino-4-methyl-1,1-di-i-propylpentanol,
(R)-2-amino-4-methyl-1,1-dicyclohexylpentanol,
(R)-2-amino-4-methyl-1,1-diphenylpentanol,
(R)-2-amino-4-methyl-1,1-di-(2-methylphenyl)pentanol,
(R)-2-amino-4-methyl-1,1-di-(3-methylphenyl)pentanol, (R)-2-amino-4-methyl-1,1-di-(4-methylphenyl)pentanol,
(R)-2-amino-4-methyl-1,1-di-(2-methoxyphenyl)pentanol,
(R)-2-amino-4-methyl-1,1-di-(3-methoxyphenyl)pentanol,
(R)-2-amino-4-methyl-1,1-di-(4-methoxyphenyl)pentanol,
1-(1-(R)-amino-3-methyl-n-butyl)cyclobutanol,
1-(1-(R)-amino-3-methyl-n-butyl)cyclopentanol,
1-(1-(R)-amino-3-methyl-n-butyl)cyclohexanol,
1-(1-(R)-amino-3-methyl-n-butyl)cycloheptanol,
(R)-2-amino-3,3-dimethyl-1,1-dimethylbutanol,
(R)-2-amino-3,3-dimethyl-1,1-diethylbutanol,
(R)-2-amino-3,3-dimethyl-1,1-di-n-propylbutanol,
(R)-2-amino-3,3-dimethyl-1,1-di-i-propylbutanol,
(R)-2-amino-3,3-dimethyl-1,1-dicyclohexylbutanol,
(R)-2-amino-3,3-dimethyl-1,1-diphenylbutanol,
(R)-2-amino-3,3-dimethyl-1,1-di-(2-methylphenyl)butanol,
(R)-2-amino-3,3-dimethyl-1,1-di-(3methylphenyl)butanol,
(R)-2-amino-3,3-dimethyl-1,1-di-(4methylphenyl)butanol,
(R)-2-amino-3,3-dimethyl-1,1-di-(2-methoxyphenyl)butanol,
(R)-2-amino-3,3-dimethyl-1,1-di-(3-methoxyphenyl)butanol,
(R)-2-amino-3,3-dimethyl-1,1-di-(4-methoxyphenyl)butanol,
1-(1-(R)-amino-2,2-dimethyl-n-propyl)cyclobutanol,
1-(1-(R)-amino-2,2-dimethyl-n-propyl)cyclopentanol,
1-(1-(R)-amino-2,2-dimethyl-n-propyl)cyclohexanol,
1-(1-(R)-amino-2,2-dimethyl-n-propyl)cycloheptanol,
(R)-2-amino-2-phenyl-1,1-dimethylethanol,
(R)-2-amino-2-phenyl-1,1-diethylethanol,
(R)-2-amino-2-phenyl-1,1-di-n-propylethanol,
(R)-2-amino-2-phenyl-1,1-di-i-propylethanol,
(R)-2-amino-2-phenyl-1,1-dicyclohexylethanol,
(R)-2-amino-2-phenyl-1,1-diphenylethanol,
(R)-2-amino-2-phenyl-1,1-di-(2-methylphenyl)ethanol,
(R)-2-amino-2-phenyl-1,1-di-(3-methylphenyl)ethanol,
(R)-2-amino-2-phenyl-1,1-di-(4-methylphenyl)ethanol,
(R)-2-amino-2-phenyl-1,1-di-(2-methoxyphenyl)ethanol,
(R)-2-amino-2-phenyl-1,1-di-(3-methoxyphenyl)ethanol,
(R)-2-amino-2-phenyl-1,1-di-(4-methoxyphenyl)ethanol,
1-(1-(R)-aminophenylmethyl)cyclobutanol,
1-(1-(R)-aminophenylmethyl)cyclopentanol,
1-(1-(R)-aminophenylmethyl)cyclohexanol,
1-(1-(R)-aminophenylmethyl)cycloheptanol,
(R)-2-amino-2-benzyl-1,1-dimethylethanol,
(R)-2-amino-2-benzyl-1,1-diethylethanol,
(R)-2-amino-2-benzyl-1,1-di-n-propylethanol,
(R)-2-amino-2-benzyl-1,1-di-i-propylethanol,
(R)-2-amino-2-benzyl-1,1-dicyclohexylethanol,
(R)-2-amino-2-benzyl-1,1-diphenylethanol,
(R)-2-amino-2-benzyl-1,1-di-(2-methylphenyl)ethanol,
(R)-2-amino-2-benzyl-1,1-di-(3-methylphenyl)ethanol,
(R)-2-amino-2-benzyl-1,1-di-(4-methylphenyl)ethanol,
(R)-2-amino-2-benzyl-1,1-di-(2-methoxyphenyl)ethanol,
(R)-2-amino-2-benzyl-1,1-di-(3-methoxyphenyl)ethanol,
(R)-2-amino-2-benzyl-1,1-di-(4-methoxyphenyl)ethanol,
1-(1-(R)-amino-2-phenyl)cyclobutanol,
1-(1-(R)-amino-2-phenyl)cyclopentanol,
1-(1-(R)-amino-2-phenyl)cyclohexanol,
1-(1-(R)-amino-2-phenyl)cycloheptanol, and
compounds having (S) configuration in the above compounds in place of (R), as well as salts of them such as hydrochloride, sulfate, acetate or the like.

The optically active 2-amino alcohol [II] described above can readily be synthesized by reacting the corresponding optically active amino acid ester or its salt such as hydrochloride, sulfate, acetate or the like with the corresponding Grignard reagent.

The optically active amino acid ester includes (R)-alanine methyl ester, (R)-valine methyl ester, (R)-leucine methyl ester, (R)-(t)-leucine methyl ester, (R)-phenylglycine methyl ester, (R)-phenylalanine methyl ester and compounds having a ethyl, propyl, n-butyl ester or other lower alkyl group in place of the methyl group in the above-described compounds.

Also usable are compounds having (S) configuration in the above-described compounds in place of (R), and salts of the above esters such as hydrochloride, sulfate, acetate and the like.

The Grignard reagent includes:
methyl magnesium chloride, ethyl magnesium chloride, isopropyl magnesium chloride, n-propyl magnesium chloride, n-butyl magnesium chloride, cyclohexyl magnesium chloride, benzyl magnesium chloride, phenyl magnesium chloride, 2-methylphenyl magnesium chloride, 3-methylphenyl magnesium chloride, 4-methylphenyl magnesium chloride, 2-methoxyphenyl magnesium chloride, 3-methoxyphenyl magnesium chloride, 4-methoxyphenyl magnesium chloride, Grignard reagent obtained by reacting magnesium with 1,3-dichloropropane, 1,4-dichlorobutane, 1,5-dichloroheptane or 1,6-dichlorohexane and compounds having bromine atoms in the above compounds in place of chlorine atoms.

The malonic acid derivative of the formula [III] includes, for example, malonic acid diester compounds such as dimethyl malonate, diethyl malonate, diethyl diethylmalonate and the like, and malonic acid halides such as malonyl dichloride, diethylmalonyl dichloride, malonyl dibromide, diethylmalonyl dibromide and the like.

The amount to be used of such compounds is usually about 0.5–2 moles, preferably about 0.5–1 mole, per mol of the opticaly active 2-amino alcohol [II].

The Lewis acid includes, for example, titanium tetraisopropoxide, aluminum triisopropoxide, dimethyltin dichloride, tin chloride, zinc chloride and the like. These Lewis acids, respectively, can be used independently or in combination of two or more.

The amount to be used of such compounds is usually about 0.001–5 moles, preferably about 0.01–1 mole, per mol of the opticaly active 2-amino alcohol [II].

In this the reaction, a solvent is usually used and such solvent includes, for example, toluene, xylene, heptane, octane, chlorobenzene, methylene chloride, dichloroethylene and so on.

These solvents, respectively, can be used independently or in combination of two or more.

The amount to be used of such compounds is not particularly limited but is usually about 2–200 parts by weight to 1 part by weight of the opticaly active 2-amino alcohol [II].

For the production of the optically active bisoxazoline compound [I] of the present invention, the bisamido alcohol [IV] is prepared according to the following process.

The optically active 2-amino alcohol [II] is usually reacted with the malonic acid diester in the above-described solvent. The reaction temperature is usually about 50–250° C., preferably about 60–180° C.

Alternatively, the optically active 2-amino alcohol [II] is usually reacted with the malonic acid dichloride in the presence of an appropriate base using the above-described solvent.

The base includes an organic base such as triethylamine, pyridine and 2,6-lutidine and the like and an inorganic base such as potassium carbonate and the like. The amount of the base to be used is usually 2 moles or more per mol of the malonic acid dichloride. The reaction temperature is usually about −30 to 100° C., preferably about −10 to 50° C.

The obtained bisamido alcohol compound [IV] may either be isolated from the reaction mixture or used in the subsequent reaction step without isolation.

The production of the optically active bisoxazoline compound [I] from the bisamido alcohol compound [IV] can be performed by methods including a method in which either the above-described amount of the Lewis acid is added after dissolving the isolated bisamido alcohol compound [IV] in the above-described solvent or is added to the reaction solution containing the bisamido alcohol compound.

The reaction temperature is usually about 50–250° C., preferably about 60–180° C.

After the reaction is completed, the optically active bisoxazoline compound [I] corresponding to the optically active 2-amino alcohol [II] used can be obtained, for example, by adding an aqueous alkali solution such as an aqueous sodium hydrogen carbonate solution to the produced reaction mixture, filtering the precipitated solid off, concentrating the filtrate, adding water, extracting the produced solution with an organic solvent such as toluene, ethyl acetate, chloroform or the like, and concentrating the obtained organic phase. The obtained optically active bisoxazoline compound [I] maybe purified by a conventional method, such as for example, distillation, column chromatography or the like. Alternatively, after the reaction is completed, the reaction solution may be concentrated and directly subjected to post-treatment such as distillation, column chromatography or the like to give the optically active bisoxazoline compound [I].

The steric configuration around the asymmetric carbon atom in the formula [I] representing the obtained optically active bisoxazoline compound is similar to that in the optically active form of the 2-amino alcohol [II] used.

The optically active bisoxazoline compound [I] includes:
methylenebis[(4R)-methyl-5,5-dimethyloxazoline],
methylenebis[(4R)-methyl-5,5-diethyloxazoline],
methylenebis[(4R)-methyl-5,5-di-n-propyloxazoline],
methylenebis[(4R)-methyl-5,5-di-i-propyloxazoline],
methylenebis[(4R)-methyl-5,5-dicyclohexyloxazoline],
methylenebis[(4R)-methyl-5,5-dimethoxyoxazoline],
methylenebis[(4R)-methyl-5,5-diethoxyoxazoline],
methylenebis[(4R)-methyl-5,5-diphenyloxazoline],
methylenebis[(4R)-methyl-5,5-di-(2-methylphenyl)oxazoline],
methylenebis[(4R)-methyl-5,5-di-(3-methylphenyl)oxazoline],
methylenebis[(4R)-methyl-5,5-di-(4-methylphenyl)oxazoline],
methylenebis[(4R)-methyl-5,5-di-(2-methoxyphenyl)oxazoline],
methylenebis[(4R)-methyl-5,5-di-(3-methoxyphenyl)oxazoline],
methylenebis[(4R)-methyl-5,5-di-(4-methoxyphenyl)oxazoline],
methylenebis[spiro{(4R)-methyloxazoline-5,1'-cyclobutane}],
methylenebis[spiro{(4R)-methyloxazoline-5,1'-cyclopentane}],
methylenebis[spiro{(4R)-methyloxazoline-5,1'-cyclohexane}],
methylenebis[spiro{(4R)-methyloxazoline-5,1'-cycloheptane}],
2,2'-methylenebis[(4R)-i-propyl-5,5-dimethyloxazoline],
2,2'-methylenebis[(4R)-i-propyl-5,5-diethyloxazoline],
2,2'-methylenebis[(4R)-i-propyl-5,5-di-n-propyloxazoline],
2,2'-methylenebis[(4R)-i-propyl-5,5-di-i-propyloxazoline],
2,2'-methylenebis[(4R)-i-propyl-5,5-dicyclohexyloxazoline],
2,2'-methylenebis[(4R)-i-propyl-5,5-diphenyloxazoline],
2,2'-methylenebis[(4R)-i-propyl-5,5-di-(2-methylphenyl)oxazoline],
2,2'-methylenebis[(4R)-i-propyl-5,5-di-(3-methylphenyl)oxazoline],
2,2'-methylenebis[(4R)-i-propyl-5,5-di-(4-methylphenyl)oxazoline],
2,2'-methylenebis[(4R)-i-propyl-5,5-di-(2-methoxyphenyl)oxazoline],
2,2'-methylenebis[(4R)-i-propyl-5,5-di-(3-methoxyphenyl)oxazoline],
2,2'-methylenebis[(4R)-i-propyl-5,5-di-(4-methoxyphenyl)oxazoline],
2,2'-methylenebis[spiro{(4R)-i-propyloxazoline-5,1'-cyclobutane}],
2,2'-methylenebis[spiro{(4R)-i-propyloxazoline-5,1'-cyclopentane}],
2,2'-methylenebis[spiro{(4R)-i-propyloxazoline-5,1'-cyclohexane}],
2,2'-methylenebis[spiro{(4R)-i-propyloxazoline-5,1'-cycloheptane}],
2,2'-methylenebis[(4R)-i-butyl-5,5-dimethyloxazoline],
2,2'-methylenebis[(4R)-i-butyl-5,5-diethyloxazoline],
2,2'-methylenebis[(4R)-i-butyl-5,5-di-n-propyloxazoline],
2,2'-methylenebis[(4R)-i-butyl-5,5-di-i-propyloxazoline],
2,2'-methylenebis[(4R)-i-butyl-5,5-dicyclohexyloxazoline],
2,2'-methylenebis[(4R)-i-butyl-5,5-diphenyloxazoline],
2,2'-methylenebis[(4R)-i-butyl-5,5-di-(2-methylphenyl)oxazoline],
2,2'-methylenebis[(4R)-i-butyl-5,5-di-(3-methylphenyl)oxazoline]
2,2'-methylenebis[(4R)-i-butyl-5,5-di-(4-methylphenyl)oxazoline],
2,2'-methylenebis[(4R)-i-butyl-5,5-di-(2-methoxyphenyl)oxazoline],
2,2'-methylenebis[(4R)-i-butyl-5,5-di-(3-methoxyphenyl)oxazoline],
2,2'-methylenebis[(4R)-i-butyl-5,5-di-(4-methoxyphenyl)oxazoline],
2,2'-methylenebis[spiro{(4R)-i-butyloxazoline-5,1'-cyclobutane}],
2,2'-methylenebis[spiro{(4R)-i-butyloxazoline-5,1'-cyclopentane}],
2,2'-methylenebis[spiro{(4R)-i-butyloxazoline-5,1'-cyclohexane}],
2,2'-methylenebis[spiro{(4R)-i-butyloxazoline-5,1'-cycloheptane}],
2,2'-methylenebis[(4R)-t-butyl-5,5-dimethyloxazoline],
2,2'-methylenebis[(4R)-t-butyl-5,5-diethyloxazoline],
2,2'-methylenebis[(4R)-t-butyl-5,5-di-n-propyloxazoline],
2,2'-methylenebis[(4R)-t-butyl-5,5-di-i-propyloxazoline],
2,2'-methylenebis[(4R)-t-butyl-5,5-diphenyloxazoline],
2,2'-methylenebis[(4R)-t-butyl-5,5-dicyclohexyloxazoline],
2,2'-methylenebis[(4R)-t-butyl-5,5-di-(2-methylphenyl)oxazoline],
2,2'-methylenebis[(4R)-t-butyl-5,5-di-(3-methylphenyl)oxazoline],
2,2'-methylenebis[(4R)-t-butyl-5,5-di-(4-methylphenyl)oxazoline],
2,2'-methylenebis[(4R)-t-butyl-5,5-di-(2-methoxyphenyl)oxazoline],
2,2'-methylenebis[(4R)-t-butyl-5,5-di-(3-methoxyphenyl)oxazoline], 2,2'-methylenebis[(4R)-t-butyl-5,5-di-(4-methoxyphenyl) oxazoline],
2,2'-methylenebis[spiro{(4R)-t-butyloxazoline-5,1'-cyclobutane}],
2,2'-methylenebis[spiro{(4R)-t-butyloxazoline-5,1'-cyclopentane}],
2,2'-methylenebis[spiro{(4R)-t-butyloxazoline-5,1'-cyclohexane}],
2,2'-methylenebis[spiro{(4R)-t-butyloxazoline-5,1'-cycloheptane}],
2,2'-methylenebis[(4R)-phenyl-5,5-dimethyloxazoline],
2,2'-methylenebis[(4R)-phenyl-5,5-diethyloxazoline],
2,2'-methylenebis[(4R)-phenyl-5,5-di-n-propyloxazoline],
2,2'-methylenebis[(4R)-phenyl-5,5-di-i-propyloxazoline],
2,2'-methylenebis[(4R)-phenyl-5,5-dicyclohexyloxazoline],
2,2'-methylenebis[(4R)-phenyl-5,5-diphenyloxazoline],
2,2'-methylenebis[(4R)-phenyl-5,5-di-(2-methylphenyl) oxazoline],
2,2'-methylenebis[(4R)-phenyl-5,5-di-(3-methylphenyl) oxazoline],
2,2'-methylenebis[(4R)-phenyl-5,5-di-(4-methylphenyl) oxazoline],
2,2'-methylenebis[(4R)-phenyl-5,5-di-(2-methoxyphenyl) oxazoline],
2,2'-methylenebis[(4R)-phenyl-5,5-di-(3-methoxyphenyl) oxazoline],
2,2'-methylenebis[(4R)-phenyl-5,5-di-(4-methoxyphenyl) oxazoline],
2,2'-methylenebis[spiro{(4R)-phenyloxazoline-5,1'-cyclobutane}],
2,2'-methylenebis[spiro{(4R)-phenyloxazoline-5,1'-cyclopentane}],
2,2'-methylenebis[spiro{(4R)-phenyloxazoline-5,1'-cyclohexane}],
2,2'-methylenebis[spiro{(4R)-phenyloxazoline-5,1'-cycloheptane}],
2,2'-methylenebis[(4R)-benzyl-5,5-dimethyloxazoline],
2,2'-methylenebis[(4R)-benzyl-5,5-diethyloxazoline],
2,2'-methylenebis[(4R)-benzyl-5,5-di-n-propyloxazoline],
2,2'-methylenebis[(4R)-benzyl-5,5-di-i-propyloxazoline],
2,2'-methylenebis[(4R)-benzyl-5,5-dicyclohexyloxazoline],
2,2'-methylenebis[(4R)-benzyl-5,5-diphenyloxazoline],
2,2'-methylenebis[(4R)-benzyl-5,5-di-(2-methylphenyl) oxazoline],
2,2'-methylenebis[(4R)-benzyl-5,5-di-(3-methylphenyl) oxazoline],
2,2'-methylenebis[(4R)-benzyl-5,5-di-(4-methylphenyl) oxazoline],
2,2'-methylenebis[(4R)-benzyl-5,5-di-(2-methoxyphenyl) oxazoline],
2,2'-methylenebis[(4R)-benzyl-5,5-di-(3-methoxyphenyl) oxazoline],
2,2'-methylenebis[(4R)-benzyl-5,5-di-(4-methoxyphenyl) oxazoline],
2,2'-methylenebis[spiro{(4R)-benzyloxazoline-5,1'-cyclobutane}],
2,2'-methylenebis[spiro{(4R)-benzyloxazoline-5,1'-cyclopentane}],
2,2'-methylenebis[spiro{(4R)-benzyloxazoline-5,1'-cyclohexane}],
2,2'-methylenebis[spiro{(4R)-benzyloxazoline-5,1'-cycloheptane}],
as well as compounds having (4S) configuration in the above compounds in place of (4R) and the like.

In addition, the bisoxazoline compounds include meso-form isomers having the (4R) configuration in the one oxazoline ring and having (4S) configuration in the other oxazoline ring in place of (4R) configuration in the above-described compounds.

The optically active cyclopropanecarboxylic acid derivative of the formula [VII] can be obtained in an industrially advantageous manner by reacting a prochiral olefin of the formula [V]:

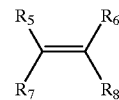

[V]

wherein $R_5$, $R_6$, $R_7$ and $R_8$ are the same or different and represent a hydrogen atom, a halogen atom, an alkyl group, an aralkyl group, an aryl group, an alkenyl group, an alkyl group substituted with a halogen atom or atoms, or an alkenyl group substituted with a halogen atom or atoms, with the proviso that when $R_5$ and $R_6$ represent the same group, then $R_7$ and $R_8$ represent different groups, with a diazoacetic acid ester of the formula [VI]:

$$N_2CHCO_2R_9 \quad [VI]$$

wherein $R_9$ represents alkyl group, cycloalkyl group or phenyl group which may be substituted, in the presence of a copper complex prepared from an optically active bisoxazoline compound [I] produced as above and a copper compound.

The copper compound used for obtaining said copper compound includes, for example, a monovalent copper compound such as copper (I) trifluoromethanesulfonate, $[Cu(CH_3CN)_4]PF_6$, $[Cu(CH_3CN)_4]ClO_4$, copper (I) acetate, copper (I) bromide, copper (I) chloride and the like, and divalent copper salts in which copper (I) moieties in the above compounds are replaced by copper (II). These can respectively be used independently or in combination of two or more. Preferably used is copper (II) trifluoromethanesulfonate, $[Cu(CH_3CN)_4]PF_6$, $[Cu(CH_3CN)_4]ClO_4$ and the like.

A solvent is usually used for the reaction of the above copper compound with the bisoxazoline ligand to obtain the copper complex, and such solvent includes, for example, halogenated hydrocarbons such as methylene chloride, 1,2-dichloroethane, chloroform, carbon tetrachloride and the like, aromatic hydrocarbons such as benzene, toluene, xylene and the like, and so on.

Alternatively, the prochiral olefin [V] to be used in the next step can be used in this step as a solvent.

The amount to be used of the solvent is usually about 50–500 parts by weight to 1 part by weight of the copper compound.

The amount to be used of the bisoxazoline compound [I] is usually about 0.8–5 moles, preferably about 1–2 moles per mol of the copper compound.

The reaction of the copper compound with the bisoxazoline compound [I] is usually carried out in an inert gas atmosphere such as argon, nitrogen or the like. From the viewpoint of the reaction yield, the above reaction is carried out in the absence of water.

The reaction temperature is not particularly limited and may usually be in a range of about 0–100° C.

In the present invention, when divalent copper compound is used for preparing the complex, it is not necessary to reduce the copper compound to a monovalent counterpart using a reducing agent such as phenylhydrazine or the like.

The copper complex obtained in this manner may be isolated or may be used as it is in the reaction of the prochiral olefin [V] and diazoacetic acid ester [VI] without isolation.

The amount to be used of the copper complex is usually about 0.0001–0.01 mol, preferably about 0.0002–0.002 mol, per mol of diazoacetic acid ester [VI], in terms of the copper compound.

Specific examples for the prochiral olefin of the formula [V] in the present invention include propene, 1-butene, isobutylene, 1-pentene, 1-hexene, 1-octene, 1-fluoro-1-chloroethene, 4-chloro-1-butene, 2-pentene, 2-heptene, 2-methyl-2-butene, 2,5-dimethyl-2,4-hexadiene, 2-methyl-2,4-hexadiene, 1-fluoro-1,1-dichloro-4-methyl-2-pentene, 2-chloro-5-methyl-2,4-hexadiene, 2-fluoro-5-methyl-2,4-hexadiene, 1,1,1-trifluoro-5-methyl-2,4-hexadiene, 2-methoxycarbonyl-5-methyl-2,4-hexadiene, 1,1-difluoro-4-methyl-1,3 -pentadiene, 1,1-dichloro-4-methyl-1,3-pentadiene, 1,1-dibromo-4-methyl-1,3-pentadiene, 1-chloro-1-fluoro-4-methyl-1,3-pentadiene, 1-fluoro-1-bromo-4-methyl-1,3-pentadiene, 1,1,1-trichloro-4-methyl-3-pentene, 1,1,1-tribromo-4-methyl-3-pentene, 2,3-dimethyl-2-pentene, 2-methyl-3-phenyl-2-butene, 2-bromo-2,5-dimethyl-4-hexene, 2-chloro-2,5-dimethyl-4-hexene, 2,5-dimethyl-6-chloro-2,4-hexadiene and the like, with 2,5-dimethyl-2,4-hexadiene being preferred.

Specific examples of $R_9$ in the diazoacetic acid [VI] used include methyl, ethyl, propyl, isopropyl, butyl, isobutyl, s-butyl, t-butyl, n-pentyl, n-hexyl, l-menthyl, d-menthyl, benzyl, cyclohexyl, phenyl, m-methylphenyl, m-methoxyphenyl, 3,5-dimethylphenyl, 3,5-dimethoxyphenyl, 4-methyl-2,6-di-t-butylphenyl and the like. Said diazoacetic acid esters [VI] can be obtained by known methods by subjecting, for example, the corresponding amino acid ester to the diazotization reaction and extracting the product with halogenated hydrocarbon such as chloroform or the like. The product can be isolated. by distillation, if necessary.

The amount of the prochiral olefin [V] to be used in the above reaction is usually 2 moles or more, preferably 5–50 moles per mol of the diazoacetic acid ester [VI].

Specific methods for reacting the prochiral olefin [V] with the diazoacetic acid ester [VI] in the presence of the copper complex include, for example, the method wherein the diazoacetic acid ester [VI] dissolved in a solvent is added to a mixture of the copper complex as obtained in the manner described above and the prochiral olefin [V].

The solvent includes, for example, halogenated hydrocarbons such as dichloromethane, 1, 2-dichloroethane, chloroform, carbon tetrachloride and the like, aliphatic hydrocarbons such as hexane, heptane, cyclohexane and the like, aromatic hydrocarbons such as benzene, toluene, xylene and the like, esters such as methyl acetate, ethyl acetate and the like.

Alternatively, the prochiral olefin [V] can be used as the solvent. These can be used in combination.

The amount to be used of the solvent is usually 2–30 parts, preferably 5–20 parts by weight to 1 part by weight of the diazoacetic acid ester [VI].

The reaction of the prochiral olefin [V] with the diazoacetic acid ester [VI] is usually carried out in an inert gas atmosphere such as argon, nitrogen or the like. From the viewpoint of the reaction yield, the above reaction is carried out in the absence of water.

The reaction temperature is not particularly limited and may be not more than the boiling point of the solvent, when used, or usually in a range of 0–100° C., preferably of 5–80° C.

The optically active cyclopropanecarboxylic acid esters [VII] obtained in the above reaction can be isolated, if necessary, by conventional methods such as distillation, column chromatography and the like.

Specific compounds belonging to the optically active cyclopropanecarboxylic acid esters [VII] obtained in the above reaction includes, for example, optically active forms of:
2-fluoro-2-chlorocyclopropanecarboxylic acid ester,
2-methylcyclopropanecarboxylic acid ester,
2,2-dimethylcyclopropanecarboxylic acid ester,
2,2-dimethyl-3-(2-methyl-1-propenyl) cyclopropanecarboxylic acid ester,
2,2-dimethyl-3-(2,2-dichloro-1-ethenyl) cyclopropanecarboxylic acid ester,
2,2-dimethyl-3-(2,2,2-trichloroethyl) cyclopropanecarboxylic acid ester,
2,2-dimethylcy3-(2,2,2-tribromoethyl) clopropanecarboxylic acid ester,
2,2-dimethyl-3 (2,2-dibromo-1-ethenyl) cyclopropanecarboxylic acid ester,
2,2-dimethyl-3-(2,2-difluoro-1-ethenyl) cyclopropanecarboxylic acid ester,
2,2-dimethyl-3-(2-fluoro-2-chloro-1-ethenyl) cyclopropanecarboxylic acid ester,
2,2-dimethyl-3-(2-fluoro-2-bromo-1-ethenyl) cyclopropanecarboxylic acid ester,
2,2-dimethyl-3-(2-fluoro-1-propenyl) cyclopropanecarboxylic acid ester,
2,2-dimethyl-3-(2-chloro-1-propenyl) cyclopropanecarboxylic acid ester,
2,2-dimethyl-3-(2-chloro-2,2,2-trifluoromethylethenyl) cyclopropanecarboxylic acid ester,
2,2-dimethyl-3-(2-methoxycarbonyl-1-propenyl) cyclopropanecarboxylic acid ester,
2,2-dimethyl-3-(2-chloro-2-methyl) propylcyclopropanecarboxylic acid ester,
2,2-dimethyl-3-(2-bromo-2-methyl) propylcyclopropanecarboxylic acid ester,
2,2-dimethyl-3-(1-propenyl)cyclopropanecarbolyic acid and the like.

The ester residue in the optically active cyclopropanecarboxylic acid esters [VII] includes, for example, methyl, ethyl, n-propyl, i-propyl, i-butyl, t-butyl, cyclohexyl, menthyl, 4-methyl-2,6-di-t-butylphenyl and the like.

The optically active cyclopropanecarboxylic acid esters [VII] obtained in such manner can be converted into optically active cyclopropanecarboxylic acids having a hydrogen atom as the substituent $R_9$ by subjecting the ester to ester hydrolysis reaction according to the known methods.

In this reaction, the optically active cyclopropanecarboxylic acid esters [VII] produced according to the reaction of the present invention can be used for the ester hydrolysis reaction without isolation.

The methods for the above described ester hydrolysis reaction are not particularly limited and may be effected according to the known process including, for example, the hydrolysis using an alkali metal hydroxide or the like, the thermal decomposition by heating in the presence of an acid catalyst and so on.

According to the present invention, the optically active cyclopropanecarboxylic acid esters [VII] can be produced in an industrially advantageous manner by reacting the prochiral olefin [V] and the diazoacetic acid ester [VI] in the presence of the copper complex prepared from the copper compound and the optically active bisoxazoline compound [I], which is the compound of the present invention and which can be synthesized from the optically active amino alcohol, which is synthesized from the optically active amino acid and the Grignard reagent.

EXAMPLES

The present invention will now be illustrated in more detail by reference of Examples, which should not be construed as a limitation upon the scope of the present invention.

Example 1

In an nitrogen atmosphere, 3.0 g (10.4 mmol) of (R)-2-amino-2-phenyl-1,1-diphenylethanol and 0.685 g (5.183 mmol) of dimethyl malonate were mixed with 150 ml of xylene and they were stirred at 120° C. for 5 hours. Then, 147 mg (0.518 mol) of titanium tetraisopropoxide was added to the reaction solution and the solution was stirred at 120° C. for 48 hours.

After the reaction was completed, xylene was evaporated and the residue was purified by column chromatography (neutral alumina; ethyl acetate/hexane=3/2) to give 2.35 g (yield: 74.1%) of 2,2'-methylenebis[(4R)-phenyl-5,5-diphenyloxazoline].

$^1$HNMR (CDCl$_3$, TMS), δ: 3.91 (s, 2H); 6.82–7.14 (m, 18H); 7.33–7.43 (m, 8H); 7.68 (d, 4H).

Example 2

The procedure in Example 1 was repeated except that (R)-2-amino-2-phenyl-1,1-diphenylethanol was replaced by 2.66 g (10.4 mmol) of (S)-2-amino-3-methyl-1,1-diphenylbutanol to give 2.15 g of 2,2'-methylenebis[(4S)-i-propyl-5,5-diphenyloxazoline] (pale yellow powders, yield: 76.5%).

$^1$HNMR (CDCl$_3$, TMS), δ: 0.64 (d, 6H, J=6.9); 0.96 (d, 6H, J=6.9); 1.70–1.85 (m, 2H); 3.64 (s, 2H); 4.63 (d, 2H, J=4.9); 7.21–7.51 (m, 20H).

Example 3

The procedure in Example 1 was repeated except that (R)-2-amino-2-phenyl-1,1-diphenylethanol was replaced by 1.72 g (10.4 mmol) of (R)-2-amino-2-phenyl-1,1-dimethylethanol to give 1.42 g of 2,2'-methylenebis[(4R)-phenyl-5,5-dimethyloxazoline] (pale yellow oil, yield: 75.4%).

$^1$HNMR (CDCl$_3$, TMS), δ: 0.88 (s, 6H); 1.60 (s, 6H); 3.53 (s, 2H); 4.90 (s, 2H); 7.20–7.35 (m, 10H).

Example 4

The procedure in Example 1 was repeated except that (R)-2-amino-2-phenyl-1,1-diphenylethanol was replaced by 1.99 g (10.4 mmol) of 1-((R)-minophenylmethyl)cyclopentanol to give 1.66 g of 2,2'-methylenebis[spiro{(4R)-phenyloxazoline-5,1'-cyclopentane}] (pale yellow oil, yield: 77.5%).

$^1$HNMR (CDCl$_3$, TMS), δ: 1.00–1.83 (m, 16H); 3.55 (s, 2H); 5.01 (s, 2H); 7.20–7.34 (m, 10H).

Example 5

Formation of Cyclopropane Ring

In a 50 ml Schlenk's tube purged with nitrogen were placed 18.05 mg (0.05 mmol) of copper trifluoromethanesulfonate, 33.6 mg (0.055 mmol) of 2,2'-methylenebis[4(R)-phenyl-5,5-diphenyloxazoline] and 10 ml of n-butyl chloride, and the mixture was stirred at room temperature for 10 minutes. After adding 6.0 g (55 mmol) of 2,5-dimethyl-2,4-hexadiene, 1.1 g (10 mmol) of ethyl diazoacetate was added dropwise at 25° C. over 2 hours. The stirring was continued at 25° C. for 1 hour after the completion of the addition of ethyl diazoacetate. The amount of produced ethyl chrysanthemum-carboxylate was found 1.44 g as determined by gas chromatography. The yield based on ethyl diazoacetate was 73.6% and the trans/cis ratio was 72/28. After evaporating 2,5-dimethyl-2,4-hexadiene (boiling point: 51° C./30 mmHg), a 1 g aliquot of the concentrated solution was taken out and subjected to alkaline hydrolysis by adding 10 ml of aqueous 1N sodium hydroxide solution and 5 ml of ethanol, and stirring at 100° C. for 1 hour. The obtained chrysanthemum-carboxylic acid was reacted with 1-menthol and the produced diastereomeric esters were analyzed by gas chromatography. The optical purity of the trans-form was 64% e.e. and the optical purity of the cis-form was 35% e.e.

Example 6

The procedure in Example 5 was repeated except that 2,2'-methylenebis[4(R)-phenyl-5,5-diphenyloxazoline] was replaced by 29.8 mg (0.055 mmol) of 2,2-methylenebis[4(R)-i-propyl-5,5-diphenyloxazoline]. The obtained amount of ethyl chrysanthemum-carboxylate was 1.21 g, the yield was 61.6% and the trans/cis ratio was 64/36. The optical purity of the trans-form was 15% e.e. and the optical purity of the cis-form was 10% e.e.

Example 7

The procedure in Example 5 was repeated except that 2,2'-methylenebis[4(R)-phenyl-5,5-diphenyloxazoline] was replaced by 19.9 mg (0.055 mmol) of 2,2-methylenebis[4(R)-phenyl-5,5-dimethyloxazoline]. The obtained amount of ethyl chrysanthemum-carboxylate was 1.54 g, the yield was 78.6% and the trans/cis ratio was 74/26. The optical purity of the trans-form was 78% e.e. and the optical purity of the cis-form was 38% e.e.

Example 8

The procedure in Example 5 was repeated except that 2,2'-methylenebis[4(R)-phenyl-5,5-diphenyloxazoline] was replaced by 22.8 mg (0.055 mmol) of 2,2-methylenebis[spiro{4(R)-phenyloxazoline-5,1'-cyclopentane}]. The obtained amount of ethyl chrysanthemum-carboxylate was 1.50 g, the yield was 76.3% and the trans/cis ratio was 74/26. The optical purity of the trans-form was 75% e.e. and the optical purity of the cis-form was 40% e.e.

Example 9

The procedure in Example 5 was repeated except that ethyl diazoacetate was replaced by 1.4 g (10 mmol) of t-butyl diazoacetate. The obtained amount of t-butyl chrysanthemum-carboxylate was 1.67 g, the yield was 74.4% and the trans/cis ratio was 79/21. Upon measurement by liquid chromatography, the optical purity of the trans-form was found 66% e.e. and the optical purity of the cis-form was found 45.2% e.e.

Example 10

The procedure in Example 9 was repeated except that 2,2'-methylenebis[4(R)-phenyl-5,5-diphenyloxazoline] was replaced by 19.9 mg (0.055 mmol) of 2,2-methylenebis[4(R)-phenyl-5,5-dimethyloxazoline]. The obtained amount of t-butyl chrysanthemum-carboxylate was 1.82 g, the yield was 81.2% and the trans/cis ratio was 85/15. The optical purity of the trans-form was 86% e.e. and the optical purity of the cis-form was 67% e.e.

Example 11

The procedure in Example 9 was repeated except that 2,2'-methylenebis[4(R)-phenyl-5,5-diphenyloxazoline] was replaced by 22.8 mg (0.055 mmol) of 2,2-methylenebis

[spiro{4(R)-phenyloxazoline-5,1'-cyclopentane}]. The obtained amount of t-butyl chrysanthemum-carboxylate was 1.76 g, the yield was 78.6% and the trans/cis ratio was 84/16. The optical purity of the trans-form was 81% e.e. and the optical purity of the cis-form was 60% e.e.

Example 12

The procedure in Example 1 was repeated except that (R)-2-amino-2-phenyl-1,1-diphenylethanol was replaced by 5.19 g (17.9 mmol) of (R)-2-amino-2-phenyl-1,1-diethylethanol to give 1.33 g of 2,2'-methylenebis[(4R)-phenyl-5,5-diethyloxazoline] (pale yellow oil, yield 38.4%).

$^1$HNMR (CDCl$_3$, TMS), δ: 0.72 (t, 6H, J=7. 2) 1.04 (t, 6H, J=7.2); 1.20–1.30 (m, 4H); 1.80–1.97 (m, 4H); 3.56 (s, 2H); 4.99 (s, 2H); 7.14–7.33 (m, 10H).

Example 13

The procedure in Example 1 was repeated except that (R)-2-amino-2-phenyl-1,1-diphenylethanol was replaced by 1.5 g (6.8 mmol) of (R)-2-amino-2-phenyl-1,1-di-n-propylethanol to give 1.08 g of 2,2'-methylenebis[(4R)-phenyl-5,5-di-n-propyloxazoline] (pale yellow powders, yield: 67.1%).

$^1$HNMR (CDCl$_3$, TMS), δ: 0.61 (t, 6H, J=6.9); 1.01 (t, 6H, J=6.9); 0.97–1.61 (m, 16H); 3.55 (s, 2H); 4.97 (s, 2H); 7.14–7.35 (m, 10H).

Example 14

The procedure in Example 5 was repeated except that 2,2'-methylenebis[4(R)-phenyl-5,5-diphenyloxazoline] was replaced by 23.0 mg (0.055 mmol) of 2,2'-methylenebis[4(R)-pheny-5,5-diethylloxazoline]. The obtained amount of ethyl chrysanthemum-carboxylate was 1.59 g, the yield was 81.2% and the trans/cis ratio was 76/24. The optical purity of the trans-form was76.3%e.e. and the optical purity of the cis-form was 45.9% e.e.

Example 15

The procedure in Example 5 was repeated except that 2,2'-methylenebis[4(R)-phenyl-5,5-diphenyloxazoline] was replaced by 26.5 mg (0.055 mmol) of 2,2'-methylenebis[4(R)-pheny-5,5-di-n-propyloxazoline]. The obtained amount of ethyl chrysanthemum-carboxylate was 1.03 g, the yield was 53.0% and the trans/cis ratio was 72/28. The optical purity of the trans-form was71.4% e.e. and the optical purity of the cis-form was 38.5% e.e.

Example 16

The procedure in Example 14 was repeated except that ethyl diazoacetate was replaced by 1.4g (10 mmol) of t-butyl diazoaxetate. The obtained amount of t-butyl chrysanthemum-carboxylate was 1.78 g, the yield was 79.6% and the trans/cis ratio was 84/16. The optical purity of the trans-form was 84.7% e.e. and the optical purity of the cis-form was 65.6% e.e.

Example 17

The procedure in Example 15 was repeated except that ethyl diazoacetate was replaced by 1.4g (10 mmol) of t-butyl diazoaxetate. The obtained amount of t-butyl chrysanthemum-carboxylate was 1.49 g, the yield was 66.5% and the trans/cis ratio was 83/17. The optical purity of the trans-form was 80.6% e.e. and the optical purity of the cis-form was 60.2% e.e.

What is claimed is:

1. An optically active isoxazoline compound of the formula [I]:

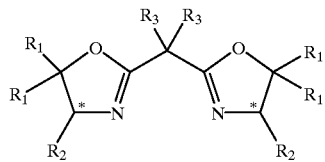

wherein

R$_1$ represents alkyl group, cycloalkyl group, aralkyl group, phenyl group which may be substituted or alkoxy group and two geminal alkyl groups may be joined together to form a cyclic structure, R$_2$ represents a phenyl group which may be substituted, R$_3$ represents hydrogen atom (C$_2$–C$_4$)alkyl group or cycloalkyl group; and asterisk * represents an asymmetric carbon atom.

2. A copper complex prepared from an optically active compound of the formula [I] as defined in claim 1 and a copper compound.

3. The copper complex according to claim 2, wherein said copper compounds is selected from the group consisting of copper (I) trifluoromethanesulfonate, [Cu(CH$_3$CN)$_4$]PF$_6$, [Cu(CH$_3$CN)$_4$]ClO$_4$, copper (I) acetate, copper (I) bromide, copper (I) chloride, copper (II) trifluoromethanesulfonate and combination thereof.

4. A process for producing the optically active bisoxazoline compound of formula [I]:

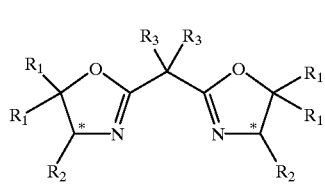

wherein R$_1$ represents alkyl group, cycloalkyl group, aralkyl group, phenyl group which may be substituted or alkoxy group and two geminal alkyl groups may be joined together to form a cyclic structure, R$_2$ represents alkyl group, cycloalkyl group, aralkyl groups, or phenyl group which may be substituted, R$_3$ represents hydrogen atom (C$_2$–C$_4$) alkyl group or cycloalkyl group; and asterisk * represents an asymmetric carbon atom;

which comprises:

reacting an optically active 2-amino alcohol of the formula [II]:

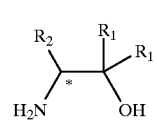

wherein R$_1$, R$_2$, and the asterisk * are as defined above, with a malonic acid derivative of the formula [III]:

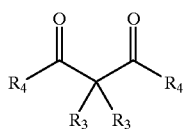

wherein $R_3$ is as defined above and $R_4$ represents alkoxy group or halogen atom, to give a bisamido alcohol compound of formula [IV]:

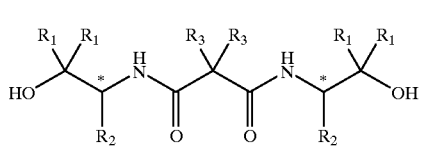

wherein $R_1$, $R_2$, $R_3$ and the asterisk * are as defined above, and then subjecting the compound of the formula [IV] to cyclization in the presence of a Lewis acid catalyst.

5. The process according to claim 4, wherein the malonic acid derivative is selected from the group consisting of dimethyl malonate, diethyl malonate, diethyl diethylmalonate, malonyl dichloride, diethylmalonyl dichloride, malonyl dibromide, diethylmalonyl dibromide.

6. The process according to claim 4, wherein the amount of the malonic acid derivative is about 0.5 to 2 moles per mol of the optically active 2-amino alcohol of formula [II].

7. The process according to claim 4, wherein the Lewis acid catalyst is selected from the group consisting of titanium tetraisopropoxide, aluminum triisopropoxide, dimethyltin dichloride, tin chloride, zinc chloride and combinations thereof.

8. The process according to claim 4, wherein the amount of Lewis acid catalyst used is about 0.001 to 5 moles per mol of the optically active 2-amino alcohol of formula [II].

9. The process according to claim 4, further comprising a solvent, the solvent is selected from the group consisting of toluene, xylene, heptane, octane, chlorobenzene, methylene chloride, dichloroethylene and combinations thereof.

* * * * *